(12) United States Patent
Williams

(10) Patent No.: US 11,291,446 B2
(45) Date of Patent: *Apr. 5, 2022

(54) SURGICAL INSTRUMENT INCLUDING AN ADAPTER ASSEMBLY AND AN ARTICULATING SURGICAL LOADING UNIT

(71) Applicant: Covidien LP, Mansfield, MA (US)

(72) Inventor: Justin Williams, North Haven, CT (US)

(73) Assignee: Covidien LP, Mansfield, MA (US)

( * ) Notice: Subject to any disclaimer, the term of this patent is extended or adjusted under 35 U.S.C. 154(b) by 169 days.

This patent is subject to a terminal disclaimer.

(21) Appl. No.: 16/718,429

(22) Filed: Dec. 18, 2019

(65) Prior Publication Data

US 2021/0186496 A1 Jun. 24, 2021

(51) Int. Cl.
*A61B 17/072* (2006.01)
*A61B 34/30* (2016.01)
*A61B 17/00* (2006.01)

(52) U.S. Cl.
CPC ........ *A61B 17/07207* (2013.01); *A61B 34/30* (2016.02); *A61B 2017/00486* (2013.01); *A61B 2017/07257* (2013.01); *A61B 2017/07271* (2013.01); *A61B 2017/07285* (2013.01)

(58) Field of Classification Search
CPC ............ A61B 17/07207; A61B 17/068; A61B 17/105; A61B 17/115; A61B 17/1114
See application file for complete search history.

(56) References Cited

U.S. PATENT DOCUMENTS

| | | |
|---|---|---|
| 2,777,340 A | 1/1957 | Hettwer et al. |
| 2,957,353 A | 10/1960 | Babacz |
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |

(Continued)

FOREIGN PATENT DOCUMENTS

| | | |
|---|---|---|
| CN | 101856251 A | 10/2010 |
| EP | 1759652 A2 | 3/2007 |

(Continued)

OTHER PUBLICATIONS

U.S. Appl. No. 16/823,901.*
European Search Report dated May 17, 2021, issued in corresponding EP Appln. No. 20215031, 7 pages.

*Primary Examiner* — Nathaniel C Chukwurah

(57) ABSTRACT

An adapter assembly includes a cam housing defining a proximal cam slot and a distal cam slot, a first elongate shaft, and a second elongate shaft. The first elongate shaft has a proximal end portion received in the proximal cam slot, and a distal end portion configured to be coupled to a surgical loading unit. The second elongate shaft has a proximal end portion received in the distal cam slot, and a distal end portion configured to be coupled to the surgical loading unit. The first and second elongate shafts are configured to move in opposing longitudinal directions in response to a rotation of the cam housing to articulate the surgical loading unit.

20 Claims, 7 Drawing Sheets

(56) References Cited

U.S. PATENT DOCUMENTS

| | | |
|---|---|---|
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,456,401 A | 10/1995 | Green et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,632,432 A | 5/1997 | Schulze et al. |
| 5,647,526 A | 7/1997 | Green et al. |
| 5,653,374 A | 8/1997 | Young et al. |
| 5,658,300 A | 8/1997 | Bito et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,766,169 A | 6/1998 | Fritzsch et al. |
| 5,779,130 A | 7/1998 | Alesi et al. |
| 5,782,396 A | 7/1998 | Mastri et al. |
| 5,782,397 A | 7/1998 | Koukline |
| 5,797,536 A | 8/1998 | Smith et al. |
| 5,820,009 A | 10/1998 | Melling et al. |
| 5,863,159 A | 1/1999 | Lasko |
| 5,865,361 A | 2/1999 | Milliman et al. |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,171,316 B1 | 1/2001 | Kovac et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,330,965 B1 | 12/2001 | Milliman et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 6,997,931 B2 | 2/2006 | Sauer et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |

(56) References Cited

U.S. PATENT DOCUMENTS

| | | |
|---|---|---|
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,819,896 B2 | 10/2010 | Racenet |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,063 B2 | 4/2011 | Zemlok et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,245,898 B2 | 8/2012 | Smith et al. |
| 8,272,554 B2 | 9/2012 | Whitman et al. |
| 8,292,150 B2 | 10/2012 | Bryant |
| 8,292,888 B2 | 10/2012 | Whitman |
| 8,303,581 B2 | 11/2012 | Arts et al. |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,752,749 B2 | 6/2014 | Moore et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 9,351,726 B2 | 5/2016 | Leimbach |
| 9,918,713 B2 | 3/2018 | Zergiebel et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0176751 A1 | 9/2004 | Weitzner et al. |
| 2004/0193146 A1 | 9/2004 | Lee et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0273135 A1 | 12/2006 | Beetel |
| 2006/0278680 A1 | 12/2006 | Viola et al. |
| 2007/0023476 A1 | 2/2007 | Whitman et al. |
| 2007/0023477 A1 | 2/2007 | Whitman et al. |
| 2007/0027468 A1 | 2/2007 | Wales et al. |
| 2007/0027469 A1 | 2/2007 | Smith et al. |
| 2007/0029363 A1 | 2/2007 | Popov |
| 2007/0055219 A1 | 3/2007 | Whitman et al. |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175956 A1 | 8/2007 | Swayze et al. |
| 2007/0175961 A1 | 8/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |

(56) References Cited

U.S. PATENT DOCUMENTS

| | | |
|---|---|---|
| 2009/0090763 A1 | 4/2009 | Zemlok et al. |
| 2009/0099876 A1 | 4/2009 | Whitman |
| 2009/0105750 A1 | 4/2009 | Price et al. |
| 2009/0108048 A1 | 4/2009 | Zemlok et al. |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0206131 A1 | 8/2009 | Weisenburgh, II et al. |
| 2009/0209990 A1 | 8/2009 | Yates et al. |
| 2009/0254094 A1 | 10/2009 | Knapp et al. |
| 2009/0314821 A1 | 12/2009 | Racenet |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0006101 A1 | 1/2011 | Hall et al. |
| 2011/0017801 A1 | 1/2011 | Zemlok et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0204119 A1 | 8/2011 | McCuen |
| 2011/0218522 A1 | 9/2011 | Whitman |
| 2011/0253765 A1 | 10/2011 | Nicholas et al. |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0223121 A1 | 9/2012 | Viola et al. |
| 2012/0234893 A1 | 9/2012 | Schuckmann et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0093149 A1 | 4/2013 | Saur et al. |
| 2013/0098966 A1 | 4/2013 | Kostrzewski et al. |
| 2013/0098968 A1 | 4/2013 | Aranyi et al. |
| 2013/0098969 A1 | 4/2013 | Scirica et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0240596 A1 | 9/2013 | Whitman |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0144970 A1 | 5/2014 | Aranyi et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236173 A1 | 8/2014 | Scirica et al. |
| 2014/0236174 A1 | 8/2014 | Williams et al. |
| 2014/0263542 A1 | 9/2014 | Leimbach et al. |
| 2014/0263554 A1 | 9/2014 | Leimbach et al. |
| 2014/0263564 A1 | 9/2014 | Leimbach et al. |
| 2014/0263565 A1 | 9/2014 | Lytle, IV et al. |
| 2014/0276932 A1 | 9/2014 | Williams et al. |
| 2014/0277017 A1 | 9/2014 | Leimbach |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0373652 A1 | 12/2014 | Zergiebel et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0157321 A1 | 6/2015 | Zergiebel et al. |
| 2015/0164502 A1 | 6/2015 | Richard et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |
| 2019/0125360 A1 | 5/2019 | Shelton, IV et al. |

FOREIGN PATENT DOCUMENTS

| | | |
|---|---|---|
| EP | 1908412 A2 | 4/2008 |
| EP | 1917929 A1 | 5/2008 |
| EP | 1952769 A2 | 8/2008 |
| EP | 2044890 A1 | 4/2009 |
| EP | 2090247 A1 | 8/2009 |
| EP | 2245994 A1 | 11/2010 |
| EP | 2329773 A1 | 6/2011 |
| EP | 2377472 A1 | 10/2011 |
| EP | 2446834 A1 | 5/2012 |
| EP | 2581055 A2 | 4/2013 |
| EP | 2612609 A2 | 7/2013 |
| EP | 2668910 A2 | 12/2013 |
| EP | 2722011 A1 | 4/2014 |
| EP | 2815705 A1 | 12/2014 |
| EP | 2823771 A1 | 1/2015 |
| EP | 2881046 A2 | 6/2015 |
| EP | 3725237 A2 | 10/2020 |
| FR | 2861574 A1 | 5/2005 |
| KR | 20120022521 A | 3/2012 |
| WO | 2008121234 A2 | 10/2008 |
| WO | 2009039506 A1 | 3/2009 |
| WO | 2009039510 A1 | 3/2009 |

\* cited by examiner

SURGICAL INSTRUMENT INCLUDING AN ADAPTER ASSEMBLY AND AN ARTICULATING SURGICAL LOADING UNIT

BACKGROUND

Technical Field

The present disclosure relates generally to surgical instruments for endoscopic use and, more specifically, to surgical instruments including adapter assemblies that articulate an attached surgical loading unit.

Background of Related Art

Various types of surgical instruments used to endoscopically treat tissue are known in the art, and are commonly used, for example, for closure of tissue or organs in transection, resection, anastomoses, for occlusion of organs in thoracic and abdominal procedures, and for electrosurgically fusing or sealing tissue.

One example of such a surgical instrument is a surgical stapling instrument. Typically, surgical stapling instruments include an end effector having an anvil assembly and a cartridge assembly for supporting an array of surgical staples, an approximation mechanism for approximating the cartridge and anvil assemblies, and a firing mechanism for ejecting the surgical staples from the cartridge assembly.

During laparoscopic or endoscopic surgical procedures, access to a surgical site is achieved through a small incision or through a narrow cannula inserted through a small entrance wound in a patient. Because of limited area available to access the surgical site, many endoscopic instruments include mechanisms for articulating the end effector of the instrument in relation to a body portion of the instrument to improve access to tissue to be treated. In addition, some end effectors have a knife shaft that translates therethrough to tissue grasped by jaws of the end effector. During articulation of the end effector, the knife shaft experiences a bending moment and/or a shear force that may inadvertently drive the knife shaft forward.

SUMMARY

In an aspect of the present disclosure, an adapter assembly includes a cam housing defining a first cam slot, an outer tube extending distally from the cam housing, and a first elongate shaft. The outer tube has a distal end portion configured to be coupled to a surgical loading unit. The first elongate shaft has a proximal end portion received in the first cam slot of the cam housing, and a distal end portion configured to be coupled to the surgical loading unit, such that the first elongate shaft translates in response to a rotation of the cam housing to articulate the surgical loading unit. The outer tube is configured to translate relative to the cam housing as the cam housing rotates.

In some aspects, the adapter assembly may further include a second elongate shaft having a proximal end portion received in a second cam slot defined by the cam housing, and a distal end portion configured to be coupled to the surgical loading unit. The first and second elongate shafts may be configured to move in opposing first and second longitudinal directions in response to a rotation of the cam housing to articulate the surgical loading unit.

In some aspects, the first and second cam slots may be configured to translate the first and second elongate shafts at a different rate from one another.

In some aspects, the adapter assembly may further include a pivot joint pivotably coupled to the distal end portion of the outer tube. The pivot joint may be configured to couple to the surgical loading unit, such that the pivot joint and the surgical loading unit translate with the outer tube.

In some aspects, the adapter assembly may further include a first link and a second link. The first link may have a proximal end portion pivotably coupled to a distal end portion of the first elongate shaft, and a distal end portion pivotably coupled to a first side of the pivot joint. The second link may have a proximal end portion pivotably coupled to a distal end portion of the second elongate shaft, and a distal end portion pivotably coupled to a second side of the pivot joint, such that the first and second links articulate the pivot joint relative to the outer tube.

In some aspects, the first cam slot may have one of a right-handed helical configuration or a left-handed helical configuration, and the second cam slot may have the other of the right-handed helical configuration or the left-handed helical configuration.

In some aspects, the first elongate shaft may have a pin extending laterally from the proximal end portion thereof into the first cam slot. The second elongate shaft may have a pin extending laterally from the proximal end portion thereof into the second cam slot.

In some aspects, the first cam slot may be a proximal cam slot and the second cam slot may be a distal cam slot.

In some aspects, each of the proximal and distal cam slots may have a helical configuration.

In some aspects, the proximal cam slot may have a proximal section having a first pitch, and a distal section having a second pitch. The distal cam slot may have a distal section having the first pitch, and a proximal section having the second pitch.

In some aspects, the second pitch may be higher than the first pitch.

In accordance with another aspect of the disclosure, a surgical instrument includes a surgical loading unit and an adapter assembly. The surgical loading unit has an end effector and a knife rod translatable through the end effector. The adapter assembly has a housing configured to be coupled to a handle assembly, a cam tube supported in the housing, an outer tube extending distally from the housing, and first and second elongate shafts. The cam tube defines a first cam slot and a second cam slot. The outer tube has a distal end portion configured to be coupled to the surgical loading unit. The first elongate shaft has a proximal end portion received in the first cam slot of the cam tube, and a distal end portion configured to be coupled to the surgical loading unit. The second elongate shaft has a proximal end portion received in the second cam slot of the cam housing, and a distal end portion configured to be coupled to the surgical loading unit. The first and second elongate shafts are configured to move in opposing first and second longitudinal directions in response to a rotation of the cam housing to articulate the surgical loading unit. The outer tube is configured to translate relative to the cam tube and with the knife rod as the cam housing rotates.

In some aspects, the surgical loading unit may be axially restrained with the outer tube, such that the outer tube and the surgical loading unit translate together and relative to the cam tube.

BRIEF DESCRIPTION OF THE DRAWINGS

Surgical instruments including embodiments of the presently disclosed adapter assemblies are disclosed herein with reference to the drawings, wherein:

FIG. 6 is a longitudinal cross-sectional view of the adapter assembly of

FIG. 4;

DETAILED DESCRIPTION

Persons skilled in the art will understand that the adapter assemblies and surgical loading units specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the described embodiments. Accordingly, the disclosure is not to be limited by what has been particularly shown and described, except as indicated by the appended claims.

As used herein, the term "distal" refers to that portion of the surgical instrument which is farthest from a clinician, while the term "proximal" refers to that portion of the surgical instrument which is closest to the clinician. In addition, as used herein, the term clinician refers to medical staff including doctors, nurses and support personnel.

The present disclosure is directed to a surgical instrument including an adapter assembly configured to be actuated by a hand-held actuator or a surgical robotic system, and a surgical loading unit coupled to the adapter assembly. The adapter assembly includes an articulation mechanism that drives an articulation of the surgical loading unit relative to the adapter assembly. The articulation mechanism includes a cam housing that defines a pair of cam slots, each of which receiving a corresponding pin of a pair of elongate shafts. As the cam housing rotates, the cam slots drive an opposing longitudinal motion of the pair of elongate shafts, which articulate the surgical loading unit. The cam slots are shaped in such a way to translate the pair of elongate shafts at a slightly different rate from one another to exert either a net proximal or net distal force on the surgical loading unit, whereby the surgical loading unit translates relative to the cam housing. In this way, when a knife rod of the surgical loading unit inadvertently translates during articulation of the surgical loading unit, the surgical loading unit will also translate therewith to negate any relative translation between the surgical loading unit and the knife rod. Additional advantages of the presently disclosed surgical instruments and components thereof are described below.

Figure 1:
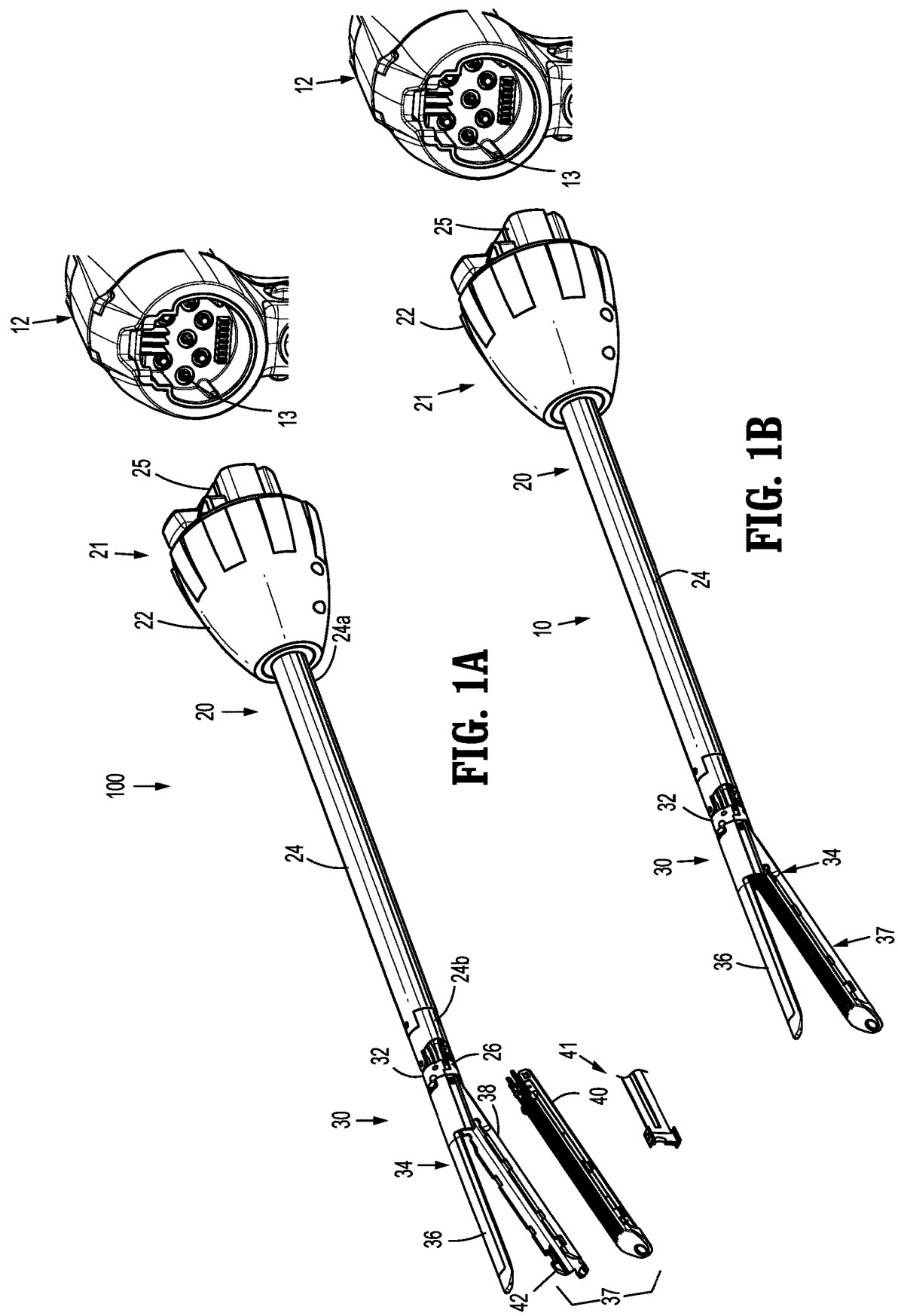
FIG. 1A is a perspective view of a surgical instrument including an adapter assembly and a surgical loading unit, with a staple cartridge body and knife rod of the surgical loading unit shown removed from the surgical loading unit.
FIG. 1B is a perspective view of the surgical instrument of FIG. 1A, with the staple cartridge body of the surgical loading unit shown installed.

FIGS. 1A and 1B illustrate a surgical instrument 10 including a handle assembly 12, an adapter assembly 20 configured to be coupled to the handle assembly 12, and a surgical loading unit 30 pivotably coupled to the adapter assembly 20. While the depicted surgical instrument 10 may be configured to fire staples, it is contemplated that the surgical instrument 10 may be adapted to fire any other suitable fastener such as clips and two-part fasteners. Additionally, while the figures depict a linear surgical stapling instrument 10, it is envisioned that certain components described herein may be adapted for use in other types of endoscopic surgical instruments including non-linear surgical stapler loading units, endoscopic forceps, graspers, dissectors, other types of surgical stapling instruments, powered vessel sealing and/or cutting devices, etc.

Figure 4:
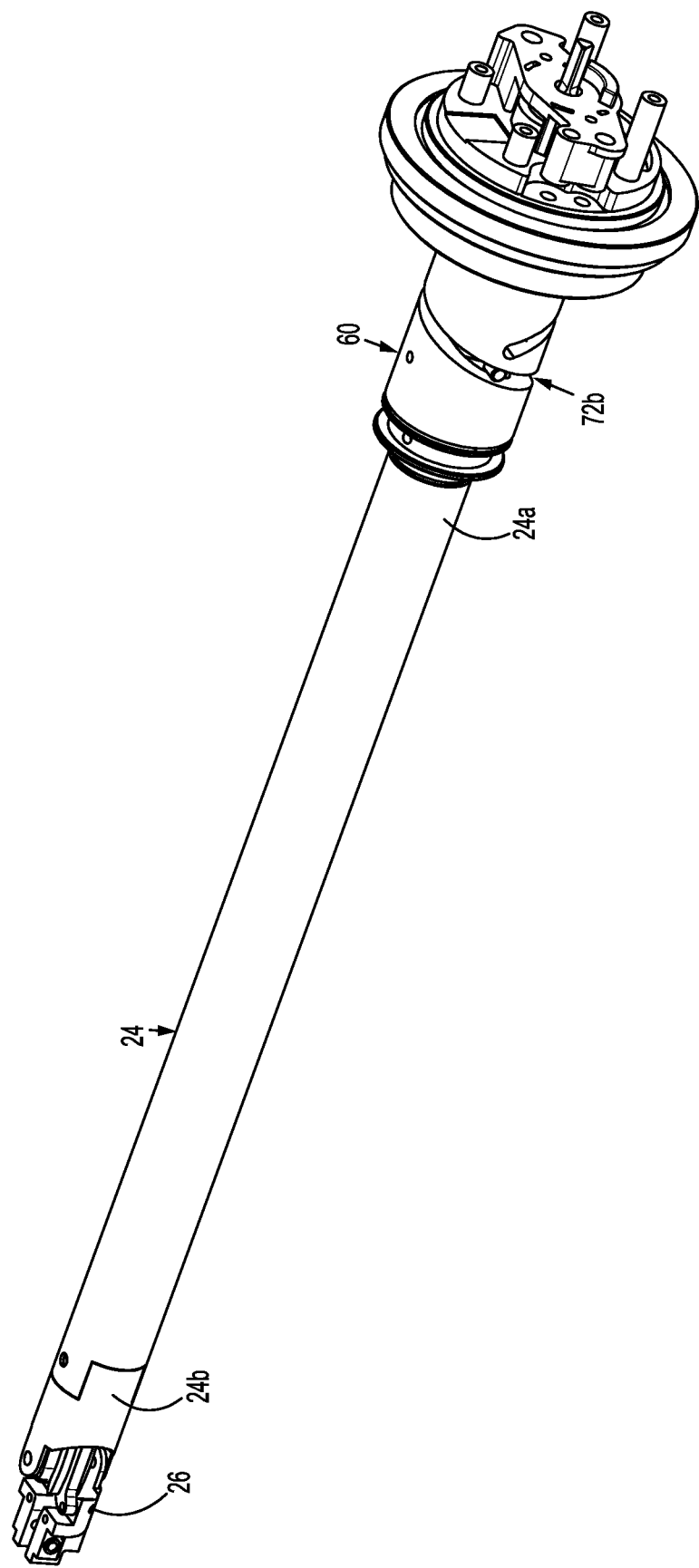
FIG. 4 is a side, perspective view of the adapter assembly of FIG. 1A illustrating a cam housing and an outer tube.
Figure 5:
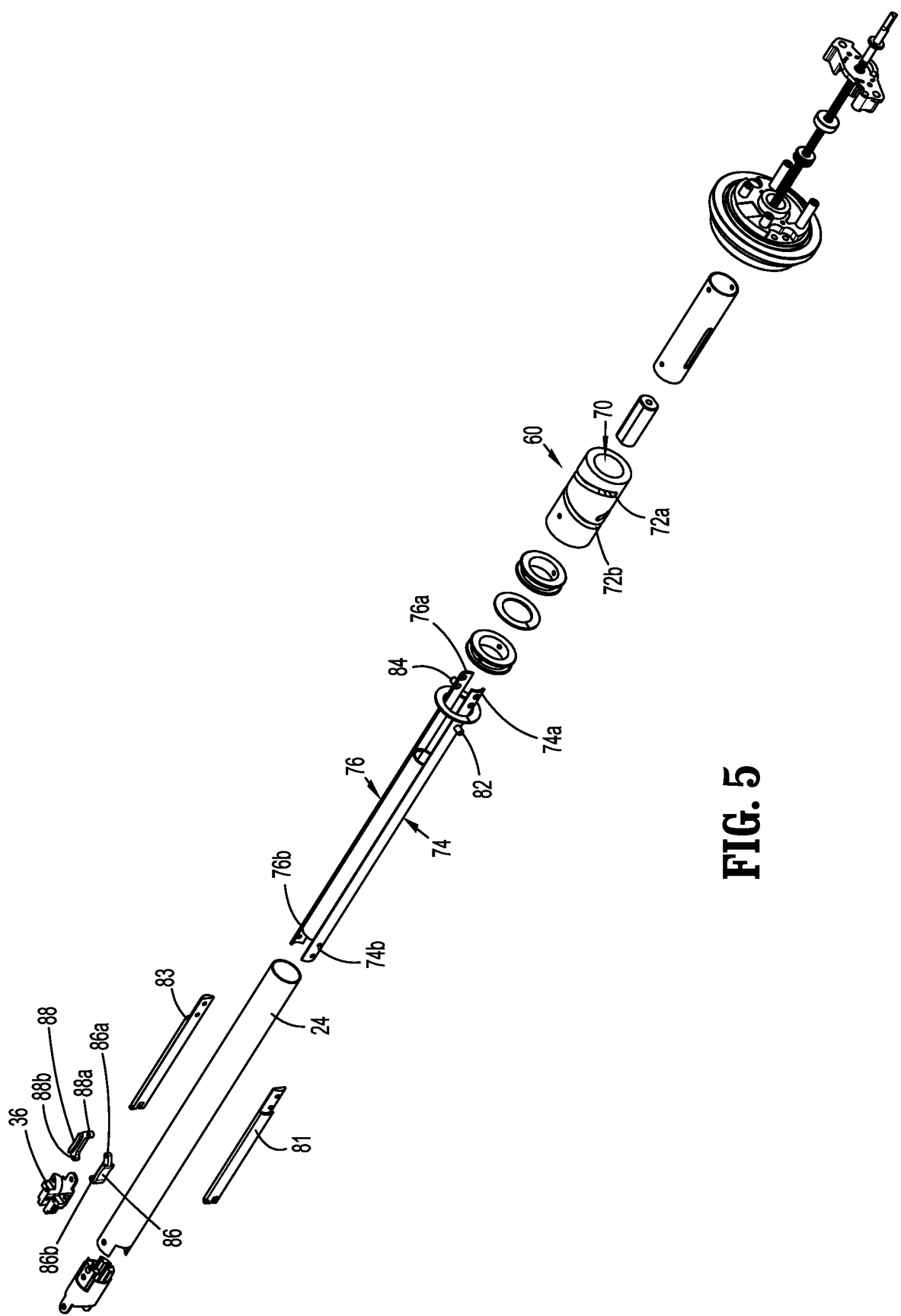
FIG. 5 is a side, perspective view, with parts separated, illustrating the internal components of the adapter assembly of FIG. 4.
Figure 6:
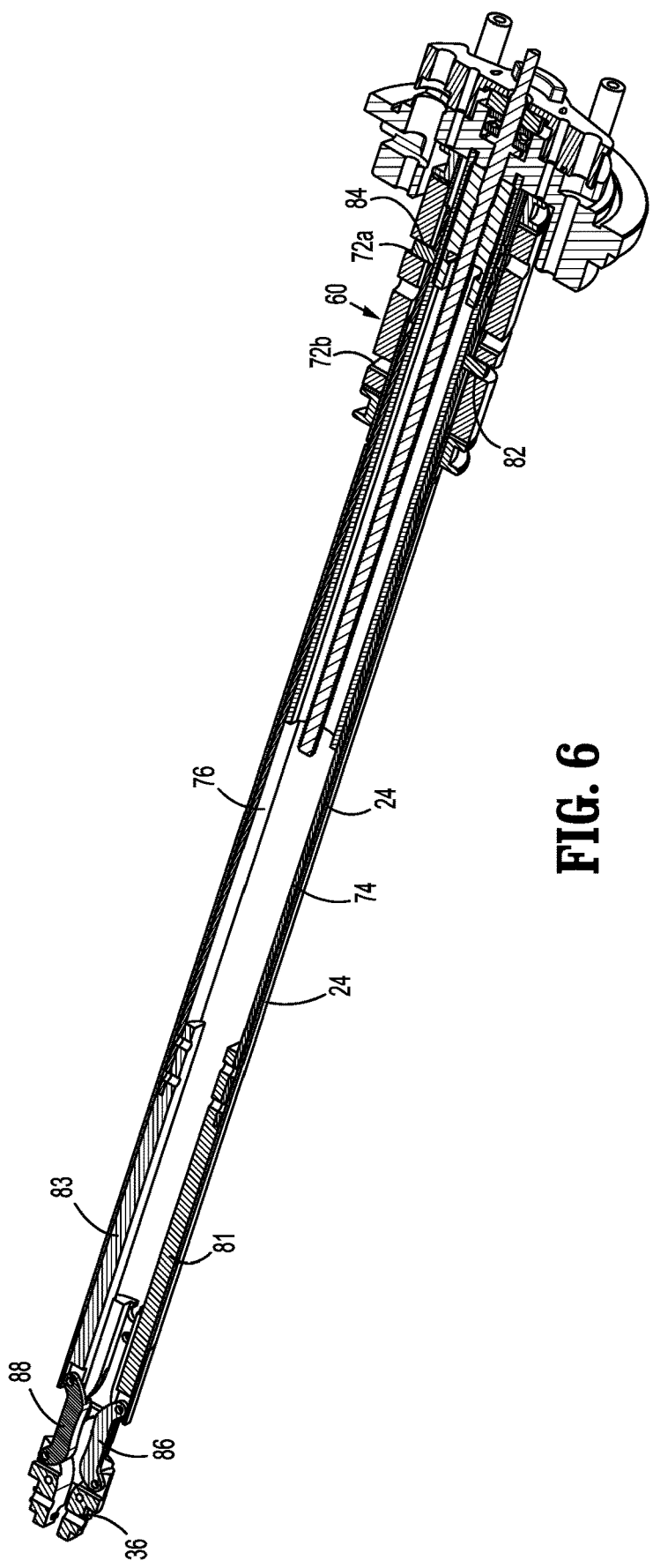
Figure 7:
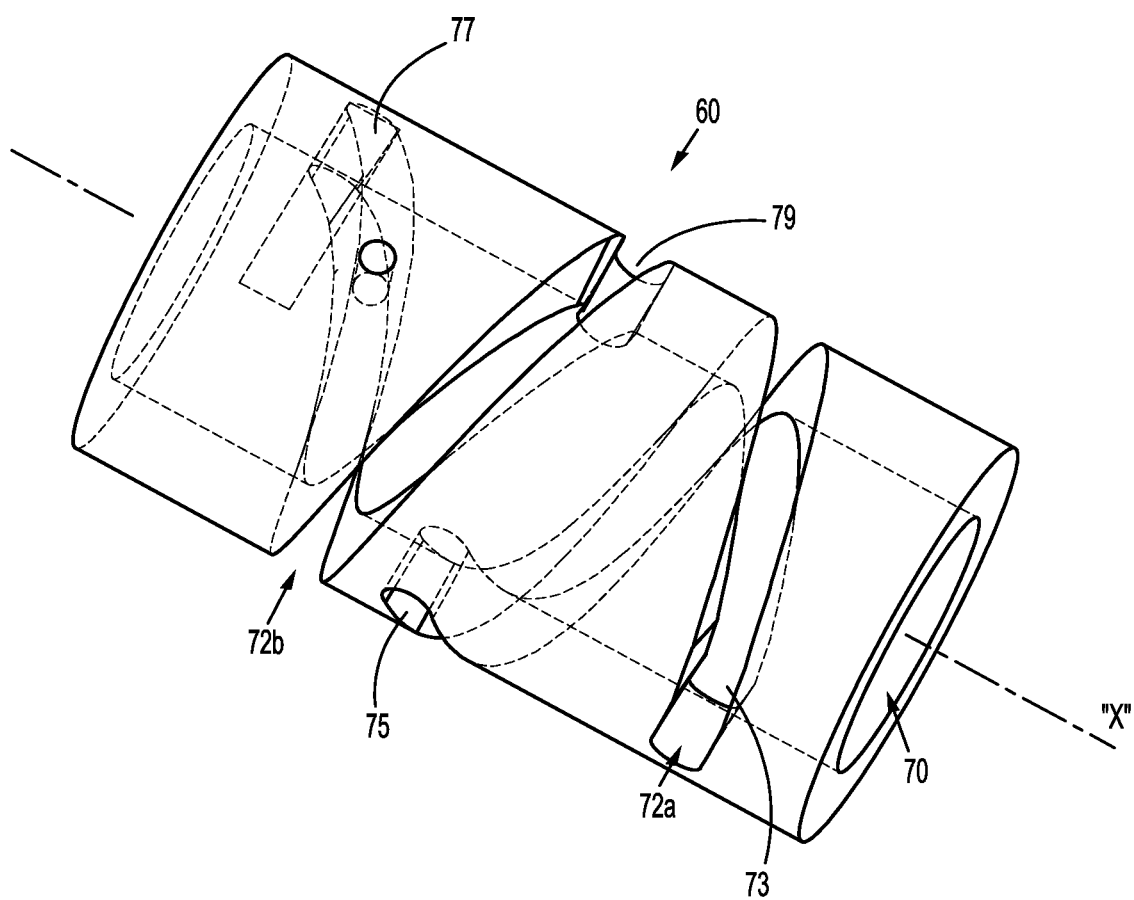
FIG. 7 is a side, perspective view, partly shown in phantom, of the cam housing of FIG. 4.

Generally, the adapter assembly 20 of the surgical instrument 10 includes an outer housing 21 and an outer tube 24 extending distally from the outer housing 21. The outer housing 21 includes a knob housing 22 and a coupling mechanism 25 extending proximally from the knob housing 22 and configured to be operably coupled to the handle assembly 12 or a surgical robotic system (not shown) responsible for actuating the surgical instrument 10. The outer tube 24 has a proximal end portion 24a slidably disposed within the distal end portion of the knob housing 22. In other embodiments, the outer tube 24 may be rotatable relative to and within the knob housing 22. The surgical loading unit 30 is adapted to be attached to a distal end portion 24b of the outer tube 24 of the adapter assembly 20 and may be configured for a single use, or may be configured to be used more than once. A pivot joint 26 (FIG. 4) is pivotably coupled to the distal end portion 24b of the outer tube 24 and axially restrained thereto. The pivot joint 26 is configured to support a collar 32 of the surgical loading unit 30 thereon, such that the outer tube 24 and the surgical loading unit 30 may translate together as an integral unit relative to the outer housing 21.

The surgical loading unit 30 includes an end effector 34 supported on the collar 32. The end effector 34 includes an anvil plate 36 non-rotationally coupled to the collar 32, and a staple cartridge assembly 37 disposed in opposed relation with the anvil plate 36. The staple cartridge assembly 37 has a chassis 38 pivotably coupled to the collar 32 and a staple cartridge body 40 configured for removable receipt in a channel 42 of the chassis 38. A knife rod 41 is translatable through the end effector 34 to cut tissue disposed therebetween. The knife rod 41 is further configured to selectively open and close the end effector 34 and fire staples therefrom as it translates through the end effector 34.

For a detailed description of the handle assembly 12, reference may be made to U.S. Pat. No. 9,918,713, filed on Nov. 21, 2014, and U.S. Patent Application Publication No. 2016/0310134, filed on Apr. 12, 2016, the entire contents of each of which being incorporated by reference herein.

Figure 2:
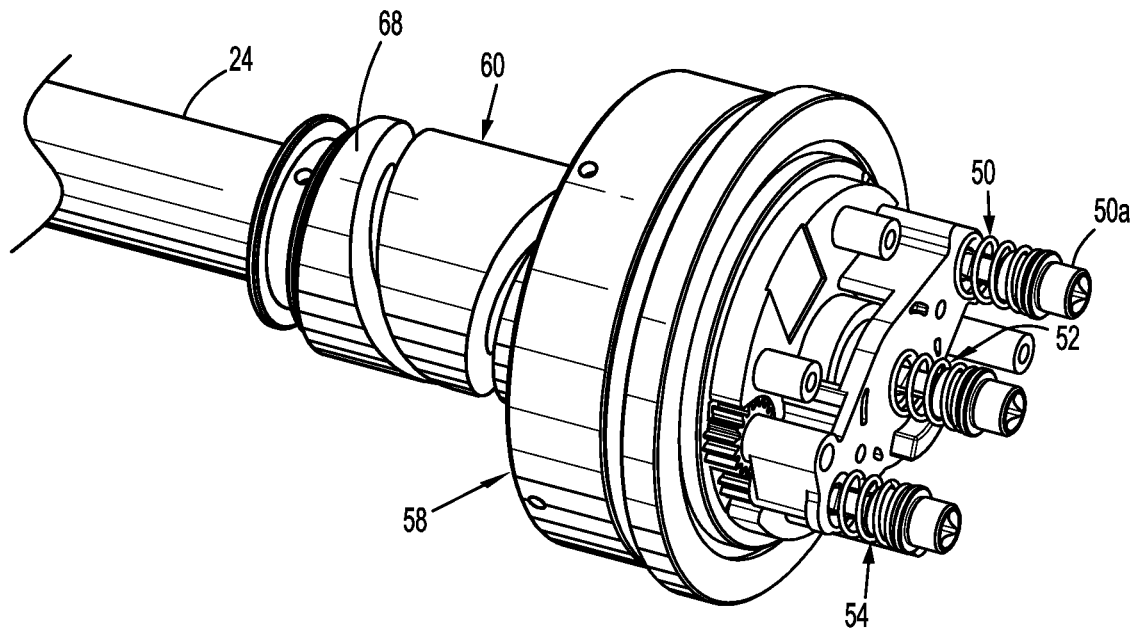
FIG. 2 is a perspective view of internal components of the adapter assembly of FIG. 1A.
Figure 3:
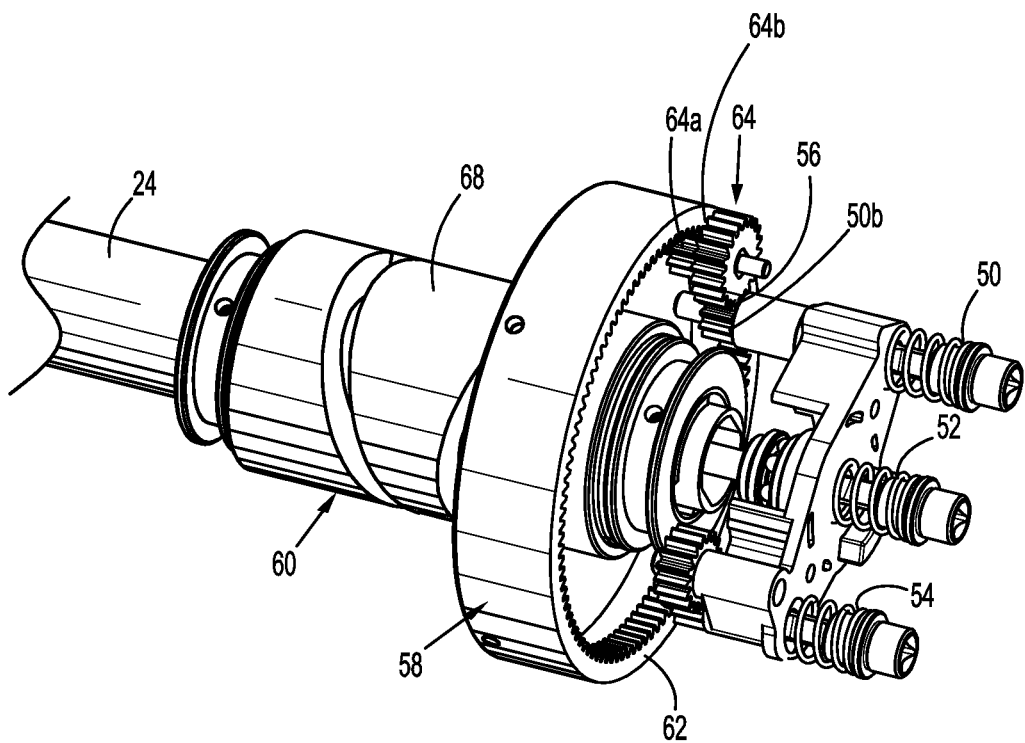
FIG. 3 is a perspective view, with parts removed, of the internal components of the adapter assembly shown in FIG. 2.

With reference to FIGS. 2 and 3, the articulation mechanism of the adapter assembly 20 will now be described. The adapter assembly 20 includes an articulation input shaft 50, a firing input shaft 52, and a rotation input shaft 54 each rotationally supported in the coupling mechanism 25 of the outer housing 21 (FIG. 1A). The articulation input shaft 50 has a proximal end portion 50a configured to be drivingly coupled to a corresponding drive member 13 of the handle assembly 12 to effect a rotation of the articulation input shaft 50. The articulation input shaft 50 has a distal end portion 50b having a gear 56 (e.g., a spur gear) fixed thereabout.

The adapter assembly 20 includes a ring gear 58 operably coupled to the articulation input shaft 50 and non-rotationally coupled to a cam housing 60. The ring gear 58 has an inner surface defining gear teeth 62 interfacing with gear teeth of a first gear 64a of a spur gear cluster 64. The spur gear cluster 64 has a second gear 64b fixed to and disposed adjacent the first gear 64a and having a larger diameter than the first gear 64a. The second gear 64b of the spur gear cluster 64 interfaces with the gear 56 non-rotationally fixed about the distal end portion 50b of the articulation input shaft 50. As such, a rotation of the articulation input shaft 50 rotates the first gear 64a and second gear 64b of the spur gear cluster 64, which, in turn, drives a rotation of the ring gear 58 and the coupled cam housing 60.

With reference to FIGS. 4-7, the cam housing 60 of the adapter assembly 20 is rotationally supported in the knob housing 22. The cam housing 60 may be pinned to the ring gear 58 (FIGS. 2 and 3), such that the cam housing 60 rotates with a rotation of the ring gear 58. The cam housing 60 defines a longitudinally-extending channel 70 therethrough dimensioned for receipt of various components of the articulation and firing mechanisms of the adapter assembly 20, thereby allowing for a more compact design of the adapter assembly 20.

The cam housing 60 defines a proximal cam slot 72a in communication with the channel 70, and a distal cam slot 72b located distally of the proximal cam slot 72a and in communication with the channel 70. The proximal and distal cam slots 72a, 72b are longitudinally spaced from one another and wrap around a central longitudinal axis "X" (FIG. 7) defined by the channel 70 of the cam housing 60. The proximal and distal cam slots 72a, 72b each have opposite helical configurations. For example, the proximal cam slot 72a may have a left-handed helical configuration, whereas the distal cam slot 72b may have a right-handed helical configuration, or vice versa. The proximal cam slot 72a has a proximal section 73 having a first pitch, and a distal section 75 having a second pitch that is higher than the first pitch. The distal cam slot 72b has a distal section 77 having the first pitch, and a proximal section 79 having the second pitch. In aspects, the proximal section 73 and the distal section 77 may have the second pitch and the distal section 75 and the proximal section 79 may have the first pitch.

The adapter assembly 20 further includes a pair of first and second axially movable elongate shafts 74, 76 and a pair of first and second articulation links 86, 88. The first and second elongate shafts 74, 76 are disposed on opposite sides of the central longitudinal axis "X" of the cam housing 60. Each of the first and second elongate shafts 74, 76 has a proximal end portion 74a, 76a disposed within the knob housing 22, and a distal end portion 74b, 76b disposed within the outer tube 24. The proximal end portion 74a of the first elongate shaft 74 has a radially-outwardly extending projection or pin 82 received within the proximal cam slot 72a. The proximal end portion 76a of the second elongate shaft 76 has a radially-outwardly extending projection or pin 84 received in the distal cam slot 72b. Due to the proximal and distal cam slots 72a, 72b of the cam housing 60 having opposing helical configurations (e.g., right-handed vs. left-handed threading), rotation of the cam housing 60 drives the first and second elongate shafts 74, 76 in opposing longitudinal directions. Further, due to the different pitches of the different sections 73, 75, 77, 79 of the cam slots 72a, 72b, the proximal and distal cam slots 72a, 72b translate the first and second elongate shafts 74, 76 at a different rate from one another, as will be described in further detail below.

The first articulation link 86 of the surgical instrument 10 has a proximal end portion 86a pivotably coupled to the distal end portion 74b of the first elongate shaft 74, and the second articulation link 88 has a proximal end portion 88a pivotably coupled to the distal end portion 76b of the second elongate shaft 76. In aspects, the first and second articulation links may be coupled to the first and second elongate shafts 74, 76 via intermediary shafts 81, 83. The first and second links 86, 88 each have a distal end portion 86b, 88b pivotably coupled to opposite sides of the collar 32 of the surgical loading unit 30. As such, the opposing longitudinal motion of the first and second elongate shafts 74, 76, induced by a rotation of the cam housing 60, pushes and pulls the corresponding first and second links 86, 88 to articulate the surgical loading unit 30 relative to the adapter assembly 20.

In operation, to articulate the surgical loading unit 30, the articulation input shaft 50 is rotated via an actuation of the handle assembly 12. The articulation input shaft 50 transfers rotational motion from the gear 56 fixed thereabout to the ring gear 58 via the spur gear cluster 64. Since the cam housing 60 is fixed to the ring gear 58, the cam housing 60 rotates with the ring gear 58 about the central longitudinal axis "X." As the cam housing 60 rotates, the proximal cam slot 72a of the cam housing 60 drives the pin 82 of the first elongate shaft 74 through the proximal cam slot 72 in a proximal direction and the distal cam slot 72b of the cam housing 60 drives the pin 84 of the second elongate shaft 76 through the distal cam slot 72b in a distal direction.

Figure 8C:
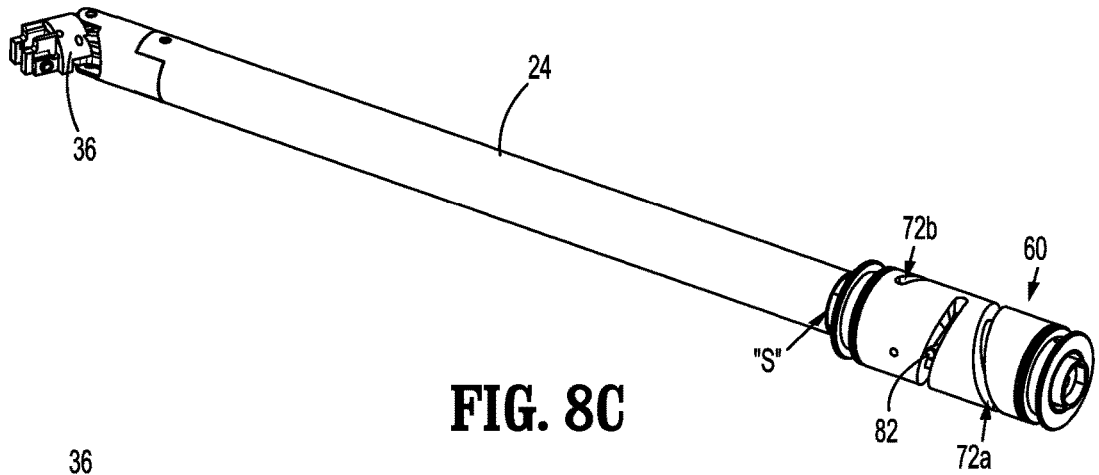
FIG. 8C is a side, perspective view of the adapter assembly of FIG. 4 with the pivot joint illustrated in a fully-articulated position.
Figure 8B:
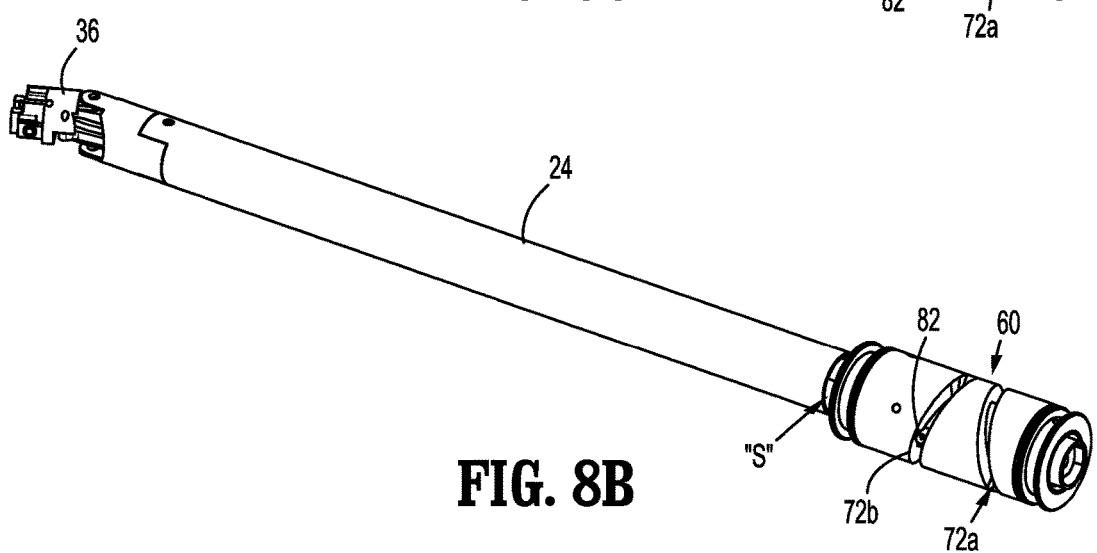
FIG. 8B is a side, perspective view of the adapter assembly of FIG. 4 with the pivot joint illustrated in a semi-articulated position.
Figure 8A:
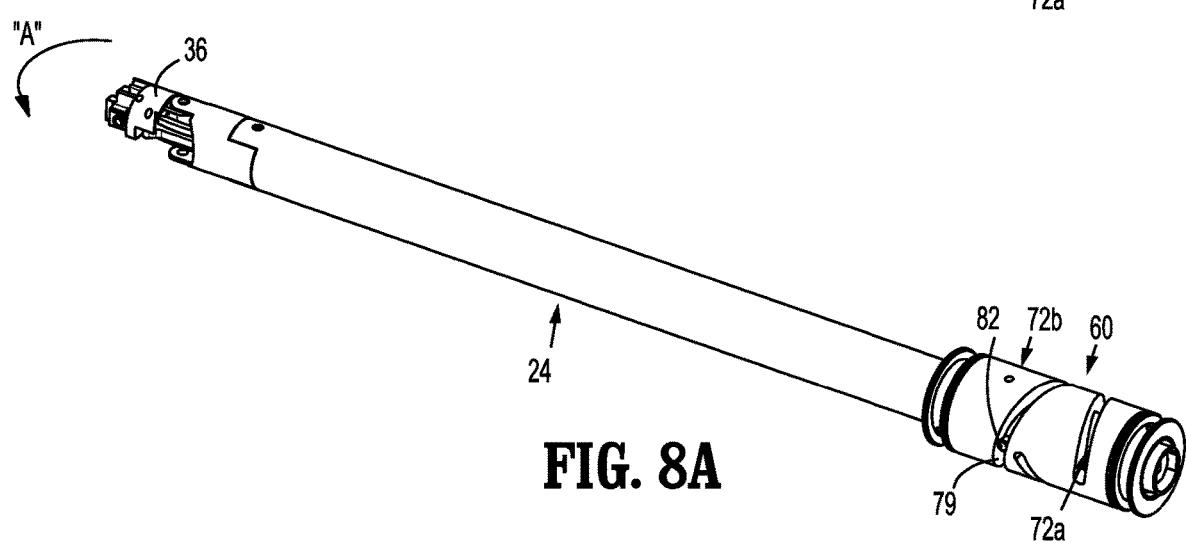
FIG. 8A is a side, perspective view of the adapter assembly of FIG. 4 with a pivot joint illustrated in a non-articulated position.

Due to the first articulation link 86 acting as a pivotable coupling between the first elongate shaft 74 of the adapter assembly 20 and the first side of the surgical loading unit 30, and the second link 88 acting as a pivotable coupling between the second elongate shaft 76 of the adapter assembly 20 and the second side of the surgical loading unit 30, proximal movement of the left elongate shaft 74 and distal movement of the right elongate shaft 76 drives an articulation of the surgical loading unit 30 in the left direction indicated by arrow "A" in FIG. 8A. It is contemplated that a rotation of the cam housing 60 in the opposite direction results in an articulation of the surgical loading unit 30 in the right direction.

During some uses, as the surgical loading unit 30 articulates relative to the outer tube 24, the knife rod 41 (FIG. 1) may be inadvertently driven distally. This may be undesirable because if the knife rod 41 advances, it may cut tissue and/or drive staples into the tissue prematurely. However, due to the profile of the proximal and distal cam slots 72a, 72b of the cam housing 60, the surgical loading unit 30 (along with the outer tube 24) is driven distally at the same rate as the knife rod 41 during articulation.

For example, as the surgical loading unit 30 articulates from coaxial with the outer tube 24 (FIG. 8A) to about 40 degrees (FIG. 8B) and to about 70 degrees (FIG. 8C), the higher pitch of the distal section 75 of the proximal cam slot 72a relative to the proximal section 79 of the distal cam slot 72b causes the right elongate shaft 76 to translate distally slightly faster than the left elongate shaft 74 translates proximally. As such, the right elongate shaft 76 exerts a net distal force on the surgical loading unit 30 (and the attached outer tube 24), to distally translate the surgical loading unit 30 (and the attached outer tube 24) relative to the cam housing 60 as evidenced by the space "S" shown in FIGS. 8B and 8C. Since the surgical loading unit 30 translates relative to the cam housing 60, any inadvertent translation of the knife rod 41 is counteracted by the concomitant translation of the end effector 30 in the same direction. Therefore, no relative motion is achieved between the knife rod 41 and the end effector 30.

Persons skilled in the art will understand that the adapter assemblies and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. An adapter assembly, comprising:
   a cam housing defining a first cam slot;
   an outer tube extending distally from the cam housing and having a distal end portion configured to be coupled to a surgical loading unit; and
   a first elongate shaft having a proximal end portion received in the first cam slot of the cam housing, and a distal end portion configured to be coupled to the surgical loading unit, such that the first elongate shaft translates in response to a rotation of the cam housing to articulate the surgical loading unit, wherein the outer tube is configured to translate relative to the cam housing as the cam housing rotates.

2. The adapter assembly according to claim 1, further comprising a second elongate shaft having a proximal end portion received in a second cam slot defined by the cam housing, and a distal end portion configured to be coupled to the surgical loading unit, wherein the first and second elongate shafts are configured to move in opposing first and second longitudinal directions in response to a rotation of the cam housing to articulate the surgical loading unit.

3. The adapter assembly according to claim 2, wherein the first and second cam slots are configured to translate the first and second elongate shafts at a different rate from one another.

4. The adapter assembly according to claim 2, further comprising a pivot joint pivotably coupled to the distal end portion of the outer tube, wherein the pivot joint is configured to couple to the surgical loading unit, such that the pivot joint and the surgical loading unit translate with the outer tube.

5. The adapter assembly according to claim 4, further comprising:
   a first link having a proximal end portion pivotably coupled to a distal end portion of the first elongate shaft, and a distal end portion pivotably coupled to a first side of the pivot joint; and
   a second link having a proximal end portion pivotably coupled to a distal end portion of the second elongate shaft, and a distal end portion pivotably coupled to a second side of the pivot joint, such that the first and second links articulate the pivot joint relative to the outer tube.

6. The adapter assembly according to claim 2, wherein the first cam slot has one of a right-handed helical configuration or a left-handed helical configuration, and the second cam slot has the other of the right-handed helical configuration or the left-handed helical configuration.

7. The adapter assembly according to claim 2, wherein the first elongate shaft has a pin extending laterally from the proximal end portion thereof into the first cam slot, and the second elongate shaft has a pin extending laterally from the proximal end portion thereof into the second cam slot.

8. The adapter assembly according to claim 2, wherein the first cam slot is a proximal cam slot and the second cam slot is a distal cam slot.

9. The adapter assembly according to claim 8, wherein each of the proximal and distal cam slots has a helical configuration.

10. The adapter assembly according to claim 9, wherein the proximal cam slot has a proximal section having a first pitch, and a distal section having a second pitch, and the distal cam slot has a distal section having the first pitch, and a proximal section having the second pitch.

11. The adapter assembly according to claim 10, wherein the second pitch is higher than the first pitch.

12. A surgical instrument, comprising:
   a surgical loading unit including:
      an end effector; and
      a knife rod translatable through the end effector; and
   an adapter assembly including:
      a housing configured to be coupled to a handle assembly;
      a cam tube supported in the housing and defining a first cam slot and a second cam slot;
      an outer tube extending distally from the housing and having a distal end portion configured to be coupled to the surgical loading unit;
      a first elongate shaft having a proximal end portion received in the first cam slot of the cam tube, and a distal end portion configured to be coupled to the surgical loading unit; and
      a second elongate shaft having a proximal end portion received in the second cam slot of the cam housing, and a distal end portion configured to be coupled to the surgical loading unit, wherein the first and second elongate shafts are configured to move in opposing first and second longitudinal directions in response to a rotation of the cam housing to articulate the surgical loading unit, wherein the outer tube is configured to translate relative to the cam tube and with the knife rod as the cam housing rotates.

13. The surgical instrument according to claim 12, wherein the first and second cam slots are configured to translate the first and second elongate shafts at a different rate from one another.

14. The surgical instrument according to claim 12, wherein the surgical loading unit is axially restrained with the outer tube, such that the outer tube and the surgical loading unit translate together and relative to the cam tube.

15. The surgical instrument according to claim 12, wherein the first cam slot has one of a right-handed helical configuration or a left-handed helical configuration, and the second cam slot has the other of the right-handed helical configuration or the left-handed helical configuration.

16. The surgical instrument according to claim 12, wherein the first elongate shaft has a pin extending laterally from the proximal end portion thereof into the first cam slot, and the second elongate shaft has a pin extending laterally from the proximal end portion thereof into the second cam slot.

17. The surgical instrument according to claim 12, wherein the first cam slot is a proximal cam slot and the second cam slot is a distal cam slot.

18. The surgical instrument according to claim 17, wherein each of the proximal and distal cam slots has a helical configuration.

19. The surgical instrument according to claim 18, wherein the proximal cam slot has a proximal section having a first pitch, and a distal section having a second pitch, and the distal cam slot has a distal section having the first pitch, and a proximal section having the second pitch.

20. The surgical instrument according to claim 19, wherein the second pitch is higher than the first pitch.

\* \* \* \* \*